(12) United States Patent
Castilho et al.

(10) Patent No.: US 12,029,774 B2
(45) Date of Patent: Jul. 9, 2024

(54) AÇAI BERRY SEED EXTRACT, FRACTIONS OF AÇAI BERRY SEED EXTRACTS, PROCESS FOR OBTAINING AÇAI BERRY SEED EXTRACTS, PHARMACEUTICAL AND FOOD COMPOSITIONS AND METHOD FOR THE TREATMENT OF DISEASES OR DISORDERS WITH AÇAI BERRY SEED EXTRACT

(71) Applicants: Power Seed Comércio e Representações Ltda, Belo Horizonte (BR); UERJ—Universidade do Estado do Rio de Janeiro, Rio de Janeiro (BR)

(72) Inventors: AndréMoreira Castilho, Belo Horizonte (BR); Luiz Francisco Pianowski, Paulínia (BR); Roberto Soares de Moura, Rio de Janeiro (BR)

(73) Assignees: Power Seed Comércio e Representações Ltda, Belo Horizonte (BR); UERJ—Universidade do Estado do Rio de Janeiro, Rio de Janeiro (BR)

( * ) Notice: Subject to any disclaimer, the term of this patent is extended or adjusted under 35 U.S.C. 154(b) by 0 days.

(21) Appl. No.: 17/867,110

(22) Filed: Jul. 18, 2022

(65) Prior Publication Data
US 2022/0347254 A1 Nov. 3, 2022

Related U.S. Application Data

(62) Division of application No. 16/359,537, filed on Mar. 20, 2019, now abandoned.

(30) Foreign Application Priority Data

Mar. 20, 2018 (BR) .................... 10 2018 005450-3
Mar. 1, 2019 (BR) .................... 10 2019 004279-6

(51) Int. Cl.
| | | |
|---|---|---|
| *A61K 36/889* | (2006.01) |
| *A23L 33/105* | (2016.01) |
| *A61K 31/216* | (2006.01) |
| *A61K 31/353* | (2006.01) |
| *A61K 31/7048* | (2006.01) |
| *A61K 45/06* | (2006.01) |
| *A61P 3/04* | (2006.01) |
| *A61P 3/06* | (2006.01) |
| *A61P 3/08* | (2006.01) |

(52) U.S. Cl.
CPC .......... *A61K 36/889* (2013.01); *A23L 33/105* (2016.08); *A61K 31/216* (2013.01); *A61K 31/353* (2013.01); *A61K 31/7048* (2013.01); *A61K 45/06* (2013.01); *A61P 3/04* (2018.01); *A61P 3/06* (2018.01); *A61P 3/08* (2018.01); *A23V 2002/00* (2013.01); *A61K 2236/333* (2013.01)

(58) Field of Classification Search
None
See application file for complete search history.

(56) References Cited

U.S. PATENT DOCUMENTS

| | | | | |
|---|---|---|---|---|
| 2011/0166226 A1* | 7/2011 | Cunha | .................. | A61P 3/10 560/60 |
| 2015/0182448 A1* | 7/2015 | Yuan | .................. | A61K 8/9789 424/195.16 |

OTHER PUBLICATIONS

De Oliveira (PLOS One (2015), vol. 10, No. 12, pp. 1-16).*
Melo (Food Chemistry (2016), vol. 213, pp. 440-449).*

* cited by examiner

*Primary Examiner* — Susan Hoffman
(74) *Attorney, Agent, or Firm* — B. Aaron Schulman, Esq.; Stites & Harbison, PLLC

(57) ABSTRACT

An açai berry seed extract (açai palm fruit, *Euterpe oleracea*) and a process for obtaining the seed extract is provided which has an effect in the treatment of diseases or disorders individually or jointly related to the metabolic syndrome. A process is also provided for obtaining an açai berry seed extract or a fraction thereof, and a pharmaceutical and a food composition is provided for treating diseases or disorders individually or jointly related to the metabolic syndrome. A method for treating diseases or disorders individually or jointly associated with metabolic syndrome in humans or animals is also provided.

5 Claims, 10 Drawing Sheets

AÇAI BERRY SEED EXTRACT, FRACTIONS OF AÇAI BERRY SEED EXTRACTS, PROCESS FOR OBTAINING AÇAI BERRY SEED EXTRACTS, PHARMACEUTICAL AND FOOD COMPOSITIONS AND METHOD FOR THE TREATMENT OF DISEASES OR DISORDERS WITH AÇAI BERRY SEED EXTRACT

CROSS-REFERENCE TO RELATED APPLICATIONS

This application is a divisional application of U.S. Ser. No. 16/359,537, filed Mar. 20, 2019, now abandoned, which claimed the benefit of Brazilian Application No. BR 10 2019 004279-6, filed on Mar. 1, 2019, and Brazilian Application No. BR 10 2018 005450-3, filed on Mar. 20, 2018, the disclosures of all of said applications being incorporated herein by reference as if set forth in their entirety.

FIELD OF THE INVENTION

The present invention is based, in its broadest scope, on açai berry seed extracts (fruit of the açai palm, *Euterpe oleracea*) with biologically active effect in the treatment of diseases or disorders individually or jointly related to the metabolic syndrome.

BACKGROUND OF THE INVENTION

The açai berry is the purple color bagasse fruit of the palm tree *Euterpe oleracea*, from the Arecaceae family used in the manufacture of food and beverages. The palm tree is native of the Amazon region of Brazil and surrounding countries, and its fruit is used as food of millennial origin by the inhabitants of that region, as "pirao" in mixture with flour or cassava or juice. More recently it has been marketed in the form of functional beverage, jams, jellies and ice creams.

The palm tree *Euterpe oleracea* is also known as *Euterpe oleracea* C. Matius, *Euterpe badiocarpa, Euterpe bradiocarpa, Catis martiana, Euterpe beardii, Euterpe cuatreasana*. Popular names are açai berry, açai berry-from-Park, açai, assai, juçara, piná, palm heart, açai berry palm tree, black açai berry, palm heart tree.

There are already in the state-of-the-art studies on açai berry pulp and oil, disclosing anti-lipidemic, cardiovascular and anti-cancer activities, in addition to contents of vitamins C, E, B1 and B2, iron, calcium and phosphorus, fibers, antioxidants like anthocyanins and alpha-tocopherol, etc.

Too much or too little is seen on the seed of açai, whose fate, except in insignificant uses such as handicrafts or coal processing, has been the pure and simple disposal, which represents an environmental problem.

However, it was found that extracts of açai berry seeds have activity on diseases or disorders individually or jointly related to the metabolic syndrome.

The metabolic syndrome is known as a group of metabolic risk factors that are manifested in a subject and increases the chances of developing heart disease, stroke and diabetes associated with obesity, also resulting from inadequate feed and inactivity. It is based on the resistance to the action of insulin, that is, insulin acts less on the tissues, forcing the pancreas to produce more insulin and raising its level in the blood.

Risk factors or the metabolic syndrome risk factors mentioned in the state of the art are, among others: abdominal obesity (excessive fat tissue around the abdomen), dyslipidemia (fat dysfunction in the blood, increased triglycerides, reduced HDL cholesterol, increased LDL cholesterol), increased blood pressure, insulin resistance and glucose intolerance (the body does not adequately use insulin and blood sugar), increased fasting glucose, liver steatosis.

The invention thus fills the need to treat, reverse and/or prevent diseases or disorders individually or jointly associated with metabolic syndrome, particularly, but not exclusively, with hypotensive action, hypoglycemic action, reducing peripheral cholesterol, reducing peripheral triglycerides, reducing total lipids, reducing visceral fat (slimming action), reducing obesity, and hepatic steatosis.

SUMMARY OF THE INVENTION

The present invention relates to the use of the açai berry seed extracts (or, commonly, açai berry's core) in the preparation of formulations having activity against diseases and disorders individually or jointly related with metabolic syndrome. It also refers to the use of açai berry seed extract in the treatment of diseases or disorders individually or jointly related to the metabolic syndrome. It further relates to compositions and formulations, pharmaceutical or food, containing extracts or components of the extracts of the açai berry's seed.

In the present invention, unless otherwise indicated, the statement "açai berry seed extract" shall be understood to include açai berry seed extract itself, fractions of said extract, or one or more of the major chemical compounds comprised in such extract.

In the present invention, unless indicated otherwise, the term "metabolic syndrome" encompasses symptoms of diseases and disorders sufficiently defining the metabolic syndrome as known in the prior art, for Example, and without excluding any other, abdominal obesity, dyslipidemia, dyslipoproteinemia, hypertriglyceridemia, hyperuricemia, increased blood pressure, insulin resistance, glucose intolerance, increased fasting glucose, and hepatic steatosis.

The present invention seeks to provide an açai berry seed extract and fractions of the extract for treating diseases and disorders individually or jointly related to the metabolic syndrome, obtained by extraction with protic polar solvent.

The present invention also seeks to provide a process for obtaining an açai berry seed extract comprising the steps of: (a) milling the açai berry seed, obtaining a powder; (b) macerating the powder in a protic polar solvent, producing a solid residue; (c) separating the solid residue, obtaining the extract, and (d) optionally drying of the extract.

The present invention seeks to provide a pharmaceutical and a food composition for treating diseases or disorders individually or jointly related to the metabolic syndrome.

The present invention also seeks to provide a method for treating diseases or disorders individually or jointly associated with metabolic syndrome in humans or animals.

DETAILED DESCRIPTION OF THE INVENTION

Figure 1:
FIG. 1 is the resulting thin layer chromatography (CCD) image of the açai berry seed extract of Example 1 (EHA), having as mobile phase ethyl acetate:acetic acid:water (100:20:30), and visualization agent R1 anisaldehyde solution.
Figure 2:
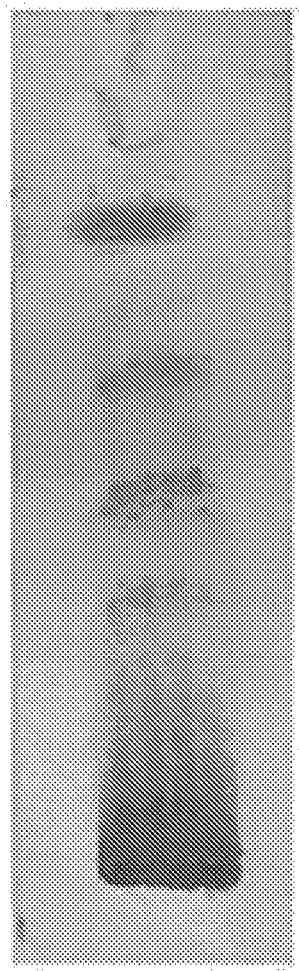
FIG. 2 is the resulting CCD image of the açai berry seed extract of Example 1, having as mobile phase ethyl acetate:acetic acid:water (100:20:30), and visualization agent R2 vanillin:50% phosphoric acid solution (1 g:100 ml).
Figure 3:
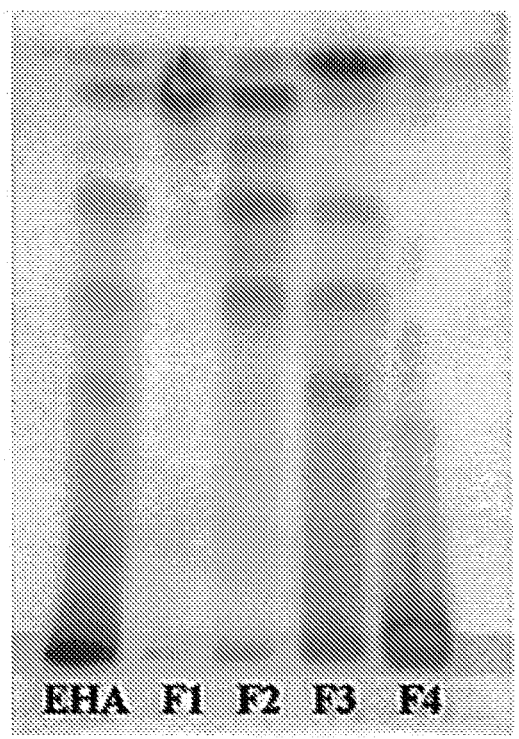
FIG. 3 is the resulting CCD image set of the extract from Example 1 and the fractions F1, F2, F3 and F4, using the same mobile phase from the previous figures and visualization agent R1 anisaldehyde solution.
Figure 4:
FIG. 4 is the resulting CCD image set of the extract from Example 1 and the fractions F1, F2, F3 and F4, using the same mobile phase from the previous figures and visualization agent R2 vanillin:50% phosphoric acid solution (1 g:100 mL).

The present invention is embodied from extracts of açai berry seeds, particularly but not exclusively, extracts with polar protic solvents, e.g. water, C1-C2 lower alcohols or mixtures thereof in hydroalcoholic solutions, as well as fractions of such extracts, or of one or more components of such extracts, mainly comprising procyanidin B2, epicatechin, rutin, catechin, vicenine 2, vitexin and chlorogenic acid. In particular, without excluding any other, the extracts of the invention are obtained from dried, milled and macerated açai berry seeds in an extraction solvent, for Example, hydroalcoholic ethanol solution, followed by separation of the solid residue, and drying of the extract (for Example by freeze drying). The drying of the obtained extract aims at the use of the dried product, for Example in powder form, at a later time, for the preparation of compositions for the treatment of metabolic syndrome.

In a particular embodiment, the invention relates to preparation of products containing açai berry seed extracts, intended for the treatment, reversal or prevention of diseases or disorders individually or jointly related to the metabolic syndrome.

In particular embodiments of the invention, there are pharmaceutical and food compositions for the treatment of diseases or disorders individually or jointly related to the metabolic syndrome characterized by comprising açai berry seed extract and one or more excipients.

The compositions of the inventions are present in solids, liquids, semi-solids or pastes, pills, tablets, hard or soft capsules, lozenges, powders (e.g. freed dried), granules, suspensions, dispersions, emulsions forms, and any other form known by the person skilled in the art. In some embodiments of the invention, such compositions may be of immediate or sustained release and may be in the form of micro or nanoparticles. They may further be in the form of liposomes, micelles or vesicles.

When the compositions of the invention are for food administration, particular forms are, for Example, in mixtures with bulk or bar cereals, shakes, juices, soft drinks, ice creams, nutraceuticals, or any form known by the person skilled in the art. Suitably, such compositions can provide effects other than that on metabolic syndrome, such as functional energy supplement or energy drink, depending on the other components of such feed composition.

As known by those skilled in the art, such compositions are formulated so as to contain the active substrate delivered according to the desired form of administration, with the aid of excipients, such as diluents, carriers or additives, which by themselves do not exhibit drug activity, but enable its administration. The following prior art publications are representative of sources known by the person skilled in the art on pharmaceutical excipients and pharmaceutical forms: "Remington: The Science and Practice of Pharmacy" (2000), 20th edition or later editions, eds. Lippincott, Williams and Wilkins; "Pharmaceutical Dosage Forms and Drug Delivery Systems" (1999), H. C. Ansel et al., 7th edition, eds. Lippincott, Williams & Wilkins, "Handbook of Pharmaceutical Excipients" (2000), A. H. Kibbe et al., 3rd edition, American Pharmaceutical Association. The compositions of the invention may further contain other biologically active compounds or substrates, which are different from those contained in the extract of the açai berry seed extract. Not limited to, such other compounds or active substrates are one or more of analgesics, anti-inflammatory, anti-diabetics, anti-lipid and anti-hypertensive, hypoglycemic, anti-cholesterolemic, anti-obesity, anti-thrombotic, anti-triglycerides, appetite suppressants, vitamins, antidepressants, anxiolytics, antibiotics, laxatives, anticonvulsants and any other known manners of the art suitable for the desired purpose.

In particular embodiments of the invention, without excluding any other, the compositions are suitable for oral or peroral, enteral or parenteral administration, including topical, transdermal, subcutaneous, intraperitoneal, intravenous, by infiltration, by inhalation, trans-mucosal, intramuscular, intrapulmonary, vaginal, rectal, intraocular and sublingual, bolus or other forms suitable for the desired administration.

In another particular embodiment, the invention relates to the treatment of diseases or disorders individually or jointly related to the metabolic syndrome in humans or animals, characterized by comprising administering a therapeutically effective amount of an açai berry seed extract.

In another embodiment, the invention relates to a method of treating diseases and disorders sufficiently defining the metabolic syndrome, comprising abdominal obesity, dyslipidemia, dyslipoproteinemia, hypertriglyceridemia, hyperuricemia, elevated blood pressure, insulin resistance, glucose intolerance, increase of fasting glycemia and hepatic steatosis of a patient, the method comprising administering in therapeutically effective amount an açai berry extract.

In another embodiment, the invention relates to a method of reducing body fat by comprising administering an effective amount of an açai berry seed extract to a patient.

EXAMPLES

Embodiments of the invention are set forth below, without limiting in any way whatsoever the extent of protection outlined in the claims set forth below.

Example 1—Obtaining Hydroalcoholic Extract (EHA) from Açai Berry Seeds 60 g of dried and milled açai berry seeds in a knife mill were transferred to a 500 ml beaker and extracted with 230 ml of 70% ethanol hydroalcohol solution in an Ultra Turrax IKA T25 apparatus 3 times, each during 3 minutes, followed by vacuum filtration in a porous plate funnel.

The seed residue was extracted in an analogous manner to the first extraction, and after filtration the seed residue was washed with 50 ml of hydroalcoholic solution.

The extracts were grouped and evaporated under vacuum to provide a dry extract.

From 60 g of dry seeds, 5.725 g of dry extract were obtained, presenting 9.54% yield.

Example 2—Fractionation and Analysis of the Extract

The dry EHA extract obtained in Example 1 was solubilized in 60 mL of distilled water and transferred to a 250 mL separator funnel, followed by the addition of 100 mL of a 50:50 mixture of hexane:ethyl acetate. After extraction and separation of the phases, the organic phase was evaporated under vacuum until complete drying yielding 25 mg of a Fraction 1 (hexane:acetate).

The aqueous phase was extracted with 100 mL of ethyl acetate in a separator funnel, followed by separation of the phases. The organic phase was evaporated under vacuum to dryness, yielding 72.0 mg of a Fraction 2 (acetate).

The aqueous phase was extracted with 100 ml of butanol in a separator funnel, followed by separation of the phases. The organic phase was evaporated under vacuum to dryness, yielding 72.0 mg of a Fraction 3 (butanol). The aqueous phase was evaporated under vacuum to dryness yielding 364 mg of a (aqueous) Fraction 4.

The dried EHA extract of Example 1 and the fractions 1 to 4 were solubilized in methanol and analyzed by thin layer chromatography (TLC) using:
  stationary phase: silica gel chromatography 60 $F_{254}$ Merck;
  mobile phase: ethyl acetate/acetic acid/water (100:20:30) by stirring the mixture and use of the upper phase;
  visualization agents: R1 anisaldehyde solution and R2 vanillin:50% phosphoric acid solution (1 g:100 mL).

After completion of the elution, the plates were evaluated in ultraviolet light (254 and 366 nm), followed by application of the visualization agents and drying in an oven at 100° C. for 5 minutes.

The results obtained from thin layer chromatography are shown in FIGS. 1 to 4.

As can be seen the higher concentration of actives appears in the EHA extract from Example 1 and in fraction 4.

Figure 5:
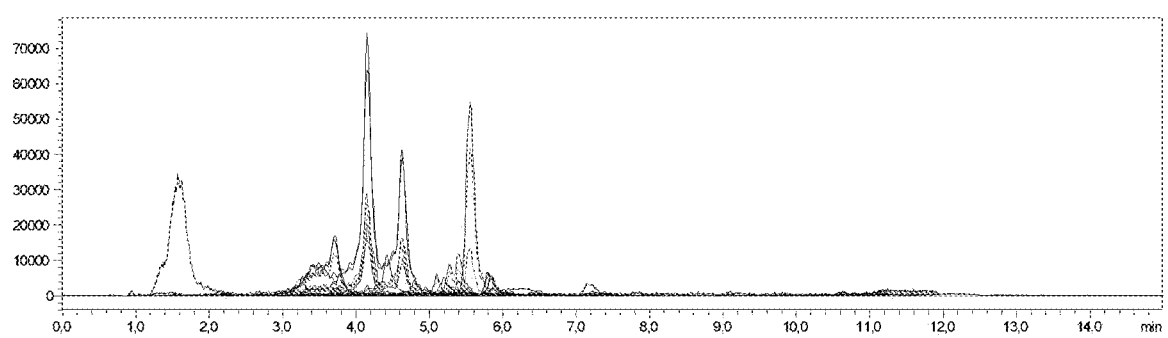
FIG. 5 is the chromatogram resulting from the MS-MS HPLC (high performance liquid chromatography/tandem mass chromatography) analysis of the EHA and F4 samples for the identification of the major components of the extract and the fractions of the açai berry seed extract.

Example 3—Identification of the Extract Components of Example 1 and its Fractions The chromatogram of the HPLC-MSMS analysis of FIG. 5, made with the extract EHA of the Example and with fraction 4, allowed to identify the following main components: procyanidin B2, epicatechin, rutin, catechin, vicenine 2, vitexin, chlorogenic acid.

This chromatogram, in view of the following in vitro artery relaxation test, points to procyanidin B2 as the compound with the highest activity, although activity is also observed with the other components.

Example 4—In Vitro Arteries Relaxation Test

The vasodilatory activity of EHA and/or its fractions was determined and quantified by ID50 (Inhibitory Dose at 50%) in preparation of the mesenteric arterial bed of male and adult Wistar mice, in vitro. After anesthesia (thiopental, 50 g/kg ip), a broad laparotomy is performed to the mice in order to expose the entire mesenteric circulation. The mesenteric artery was isolated and cannulated with cannula and polyethylene. Immediately 1 to 2 ml of Krebs nourishing solution with heparin was injected in order to avoid mesenteric intravascular coagulation. The mesenteric vascular bed was dissected, placed in a heated tub and perfused with Krebs solution at 37° C., by peristaltic pump (4 ml/minute). The perfusion pressure was recorded continuously in computer, through program (PowerLab 4/30). After a period of equilibration, it was added (30 μM) noradrenaline in the Krebs fluid in order to raise the vascular tone of the mesenteric vascular bed. Once the noradrenaline constant pressure response was obtained in the mesenteric vascular bed, increasing doses of EHA and/or fractions in the mesenteric vascular bed were injected. Perfusion pressure reductions induced by extracts and/or fractions were analyzed by the computer and expressed as reduction percent of noradrenaline-induced pressure response. The doses of EHA and/or fractions that reduce 50% of the maximal noradrenaline pressure response correspond to the ID50 of the EHA and/or fractions, considering that the lower the ID50, the greater the vasodilatory activity of EHA and/or its fractions.

The graphs of FIGS. 6a-6f show the vasodilatory effect of increasing doses of EHA from Example 1 (FIG. 6a) and from fractions F1 to F4 (FIGS. 6b, 6c, 6d, 6e) of Example 2 on the perfusion pressure of the mesenteric vascular bed of mice and their respective ID.

Figure 6A:
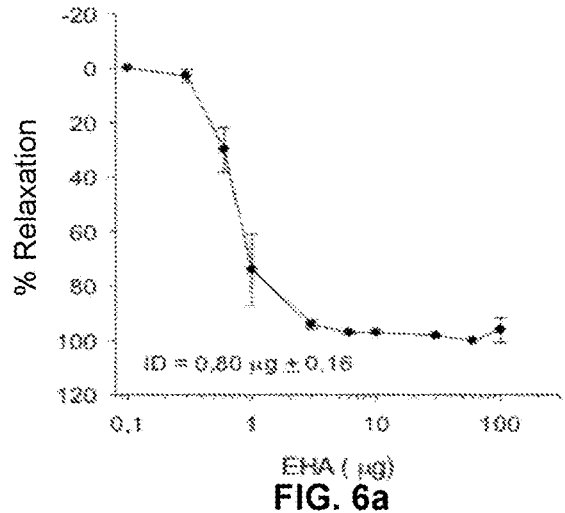
FIGS. 6a-6f are graphs, which evaluates the vasodilatory activity of EHA obtained in Example 1 and its fractions (F1, F2, F3, and F4) obtained according to Example 2, in the mesenteric vascular bed of mice by the in vitro method.
Figure 6B:
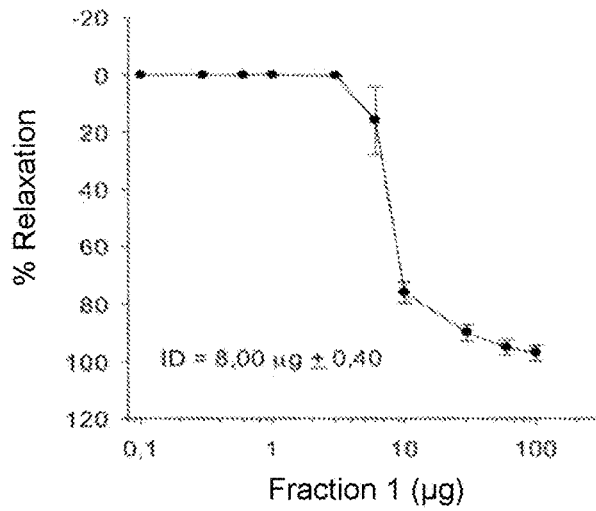
Figure 6C:
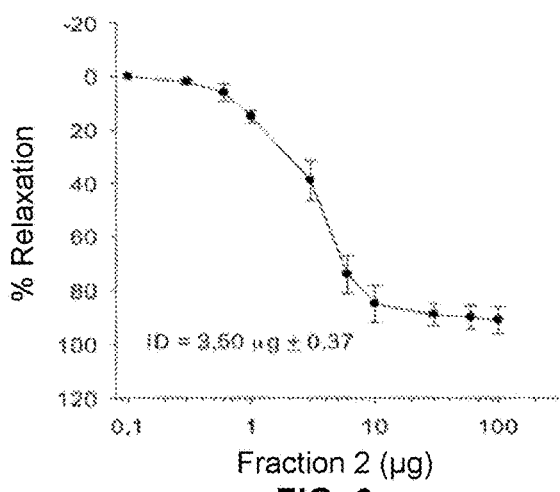
Figure 6D:
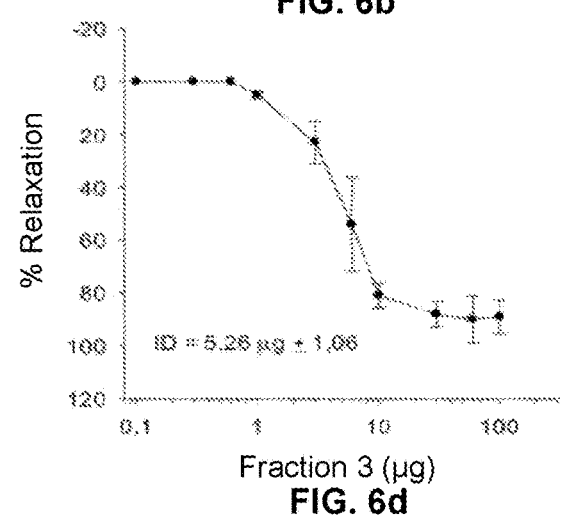
Figure 6E:
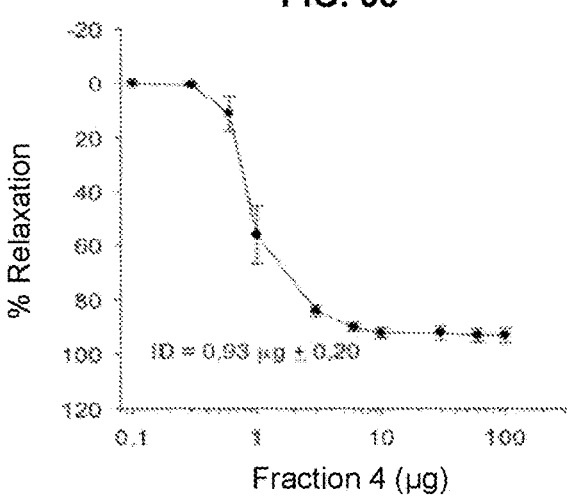
Figure 6F:
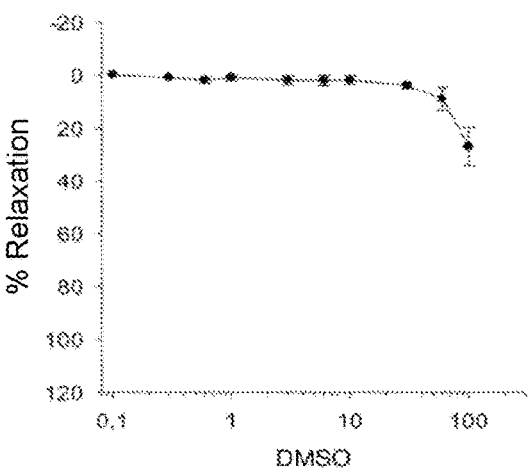

FIG. 6f shows the same test made with dimethylsulfoxide (DMSO) used as a solvent of Fraction 1, which was not water soluble, as a comparison parameter. It can be noticed that the % relaxation is very low in relation to the other samples.

The analysis of FIG. 6a demonstrates the intense vasodilatory activity of EHA on mice mesenteric vessels, and further the dose that produces 50% inhibitory effect on noradrenaline-induced vasoconstriction is the lowest among all tested in this experimental model, suggesting higher activity than the fractions studied.

It can be seen in FIG. 6f that DMSO was practically inactive in inducing vasodilatory effect and that the other fractions presented vasodilatory activity, mainly fraction 4, whose ID50 was very close to the ID50 of the EHA.

FIGS. 6a and 6e, together with the CCD of the samples from the EHA extract of Example 1 and F4 fraction of such extract, from Example 2, point out to the greater activity of procyanidin B2.

Example 5—Antihypertensive Activity Test

Blood pressure (systolic and diastolic) was measured in the tail by non-invasive method. After a period of adaptation to the blood pressure recording method (2 weeks), the animals were divided into two groups of 5 mice, one treated orally (gastric gavage) with EHA at a dose of 200 mg/kg/day and the other group orally treated (gastric gavage) with distilled water. The antihypertensive effect of EHA assessed on blood pressure of non-anesthetized spontaneously hypertensive adult male mice (SHR) is illustrated in FIG. 7.

The points in the curves refer to systolic and/or diastolic blood pressure values, and are expressed as mean±standard error of the mean. During the initial period of adaptation of the mice to the blood pressure measurement method, from 0.5 to 2 weeks, the values refer to a single group of 10 animals. At the end of 2 weeks, the hypertensive animals were randomly divided into two groups of 5 animals, one group being treated daily (gastric gavage) with 200 mg/kg EHA diluted in distilled water and the other group treated daily with distilled water (control) for another 2 weeks. The "*" symbol represents the statistically significant difference (t Student) between the control group and EHA treated animals.

Figure 7:
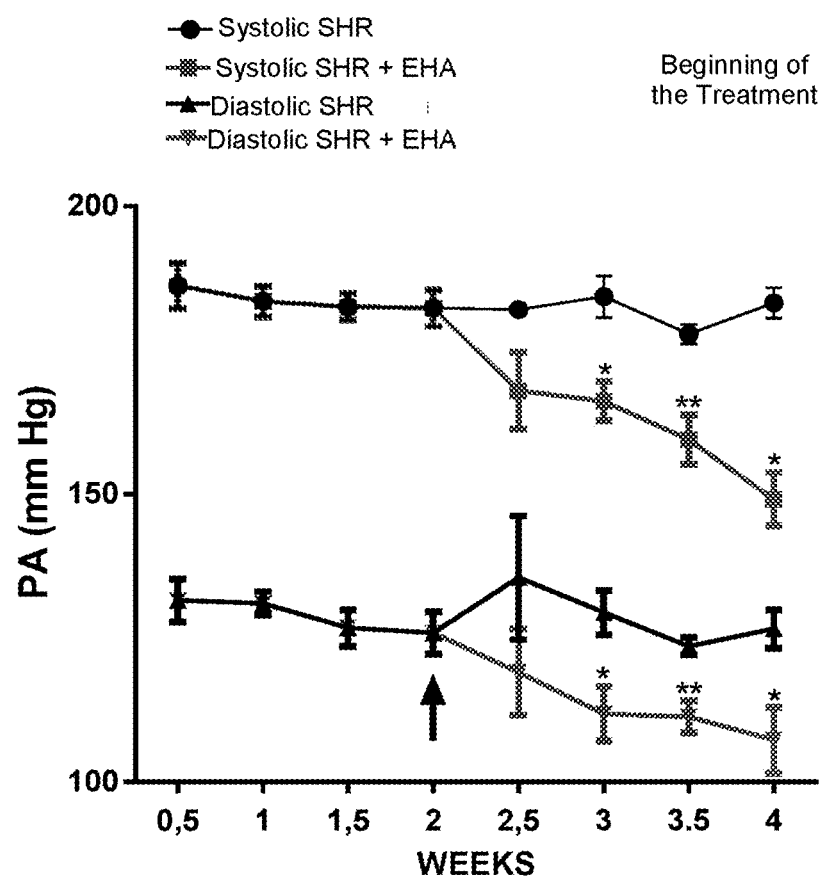
FIG. 7 represents the antihypertensive activity of EHA in adult mice with spontaneous arterial hypertension (SHR).

The analysis of FIG. 7 shows, in spontaneously hypertensive mice (SHR), a significant (Student t-test) antihypertensive action of EHA at a dose of 200 mg/kg/day, compared to the control treatment with distilled water by the oral route (gavage).

Example 6—Metabolic Parameter Tests

The tests were carried out for verifying the effects of EHA on metabolic parameters such as body weight gain, visceral (epididimal and retroperitoneal) adipose tissue weight, plasma cholesterol, plasma LDL, glucose, oral glucose tolerance test (OGTT), liver triglyceride and liver weight were observed in mice submitted to a hyper-lipid diet containing lard (278 g/kg feed) or normal diet (zero lard) for 90 days.

Experiments were performed on male C57BL/6 mice being 20 to 30 days old with body weight between 20 to 25 g. After a period of adaptation to the vivarium, 30 mice were divided into three groups: control fed with a normal diet (C), fed with a hyper-lipid diet (HL), and fed with a hyper-lipid diet plus EHA treatment at a dose of 300 mg/kg/day per gavage (HL+EHA) for 90 days. Prior to the initiation of EHA administration, the animals were weighed and a blood glucose dosage was measured using an automatic meter (ACCU CHEC-ACTIVE, ROCHE) based on the glucose-glucose oxidase reaction. The body weight was assessed before and throughout the experimental period. Days before the end of the experimental period, glucose (2 g/kg) was applied orally and glycemia was measured in the tail blood of the mice at 0, 15, 30 and 60 minutes after the application of glucose to evaluate the oral test of glucose tolerance. At the end of 90 days of treatment the mice were sacrificed and blood, adipose tissue and liver were collected for the biochemical analyzes and weight of the tissues studied. The lipid profile was analyzed in the plasma by commercial kit by colorimetric method.

Figure 8A:
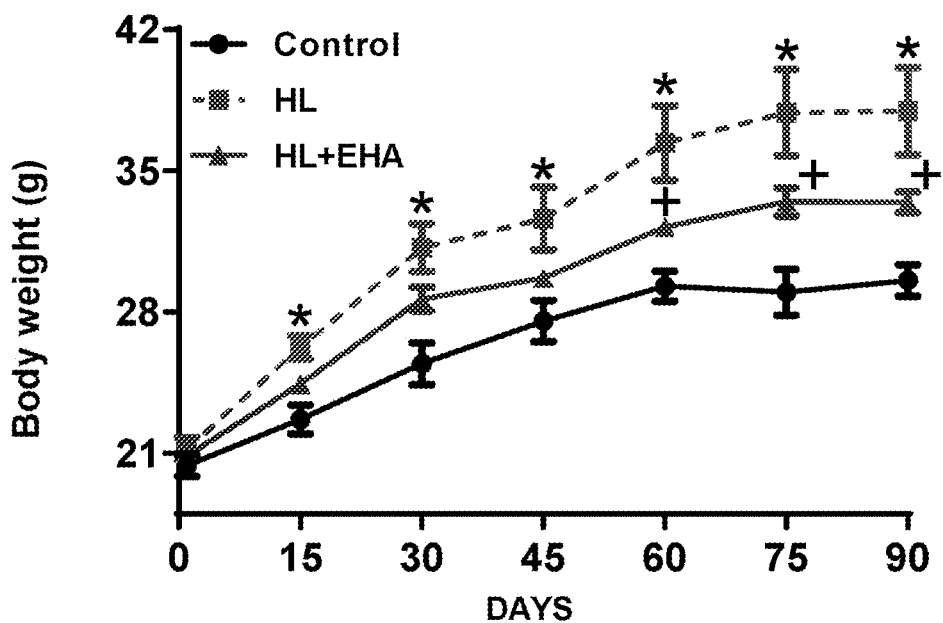
FIGS. 8a to 8h depict the effects of EHA on metabolic parameters such as: body weight gain, visceral adipose tissue weight (epididimal and retroperitoneal), plasma cholesterol, plasma LDL, glucose, oral glucose tolerance test (OGTT), hepatic triglyceride and liver weight.

FIG. 8a shows the significant anti-obesity effect of EHA (300 mg/kg/day) applied by gastric gavage in C57BL/6 mice undergoing a hyper-lipid diet over 90 days. Values are expressed as mean±standard error of the mean, n=9 male mice in the control and HL groups; n=12 mice in the HL+EHA group. Significant differences between groups are indicated by the symbols: "*" p<0.05 in relation to the control group; "+" p<0.05 compared to the HL group; as determined by the one-way ANOVA method and Tukey's post-test.

Figure 8B:
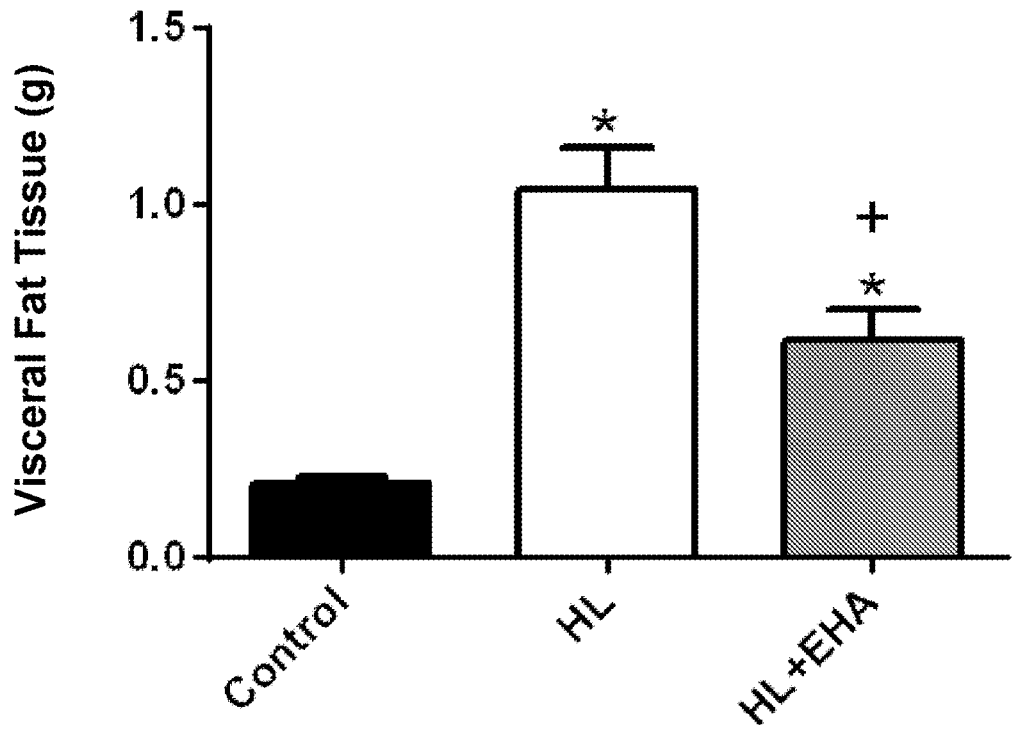

FIG. 8b shows the significant effect of EHA (300 mg/kg/day, by gastric gavage) on reducing the weight gain of visceral adipose tissue in C57BL/6 mice fed with a high fat diet over a 90-day period. Values are expressed as mean±standard error of the mean, n=9 male mice in the control and HL groups; n=12 mice in the HL+EHA group. Significant differences between groups are indicated by the symbols: "*" p<0.05 in relation to the control group; "+" p<0.05 compared to the HL group; as determined by the one-way ANOVA method and Tukey's post-test.

Figure 8C:
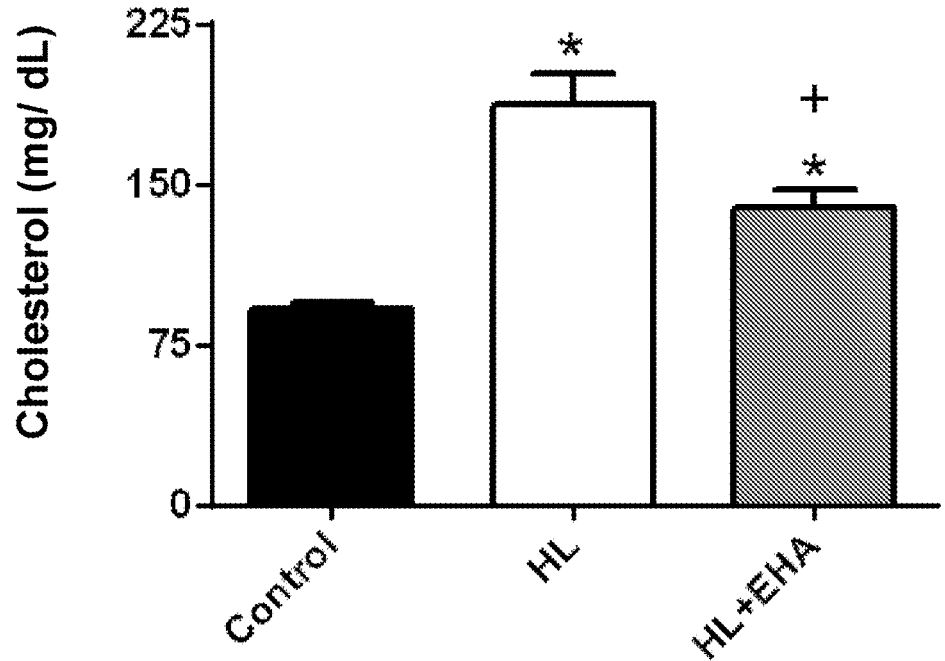

FIG. 8c shows that the increase in plasma cholesterol levels induced by the hyper-lipid diet over 90 days in C57BL/6 mice is significantly reduced by the action of EHA at the dose of 300 mg/kg/day, applied by gastric gavage. Values are expressed as mean±standard error of the mean, n=9 male mice in the control and HL groups; n=12 mice in the HL+EHA group. Significant differences between groups are indicated by the symbols: "*" p<0.05 in relation to the control group; "+" p<0.05 compared to the HL group; as determined by the one-way ANOVA method and Tukey's post-test.

Figure 8D:
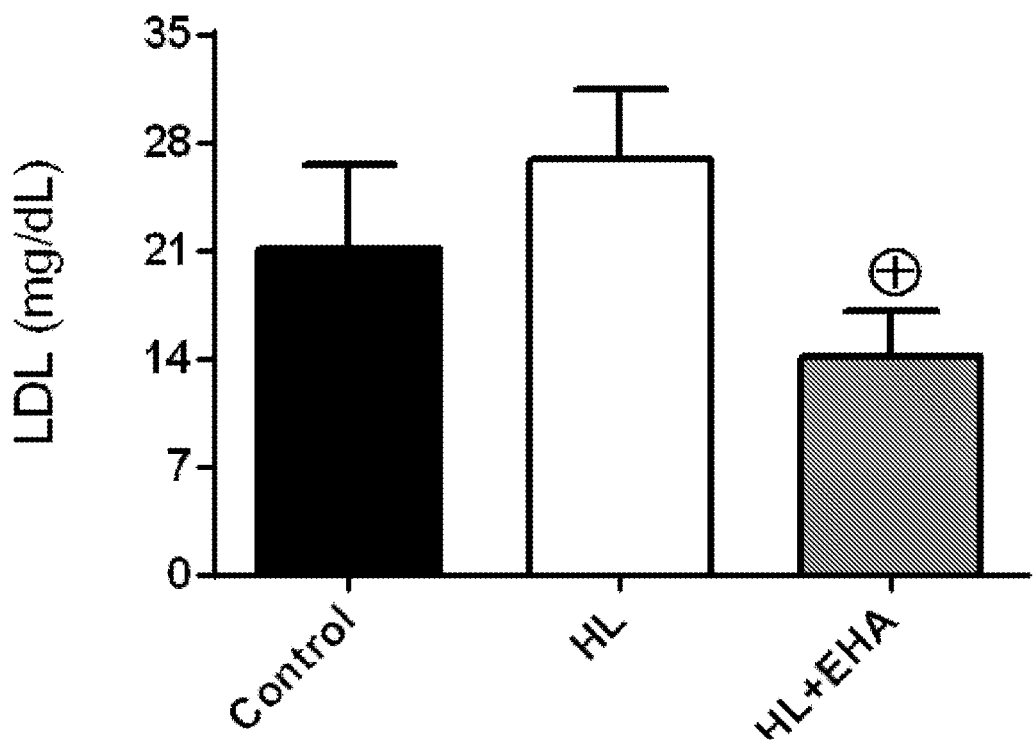

FIG. 8d shows that the increase in plasma LDL levels induced by the hyper-lipid diet over 90 days in C57BL/6 mice is significantly reduced by the action of EHA at the dose of 300 mg/kg/day applied by gastric gavage. Values are expressed as mean±standard error of the mean, n=9 male mice in the control and HL groups; n=12 mice in the HL+EHA group. Significant difference between the groups are indicated by the symbol "⊕" p<0.05 compared to the HL group; as assessed by the unpaired t Student test.

Figure 8E:
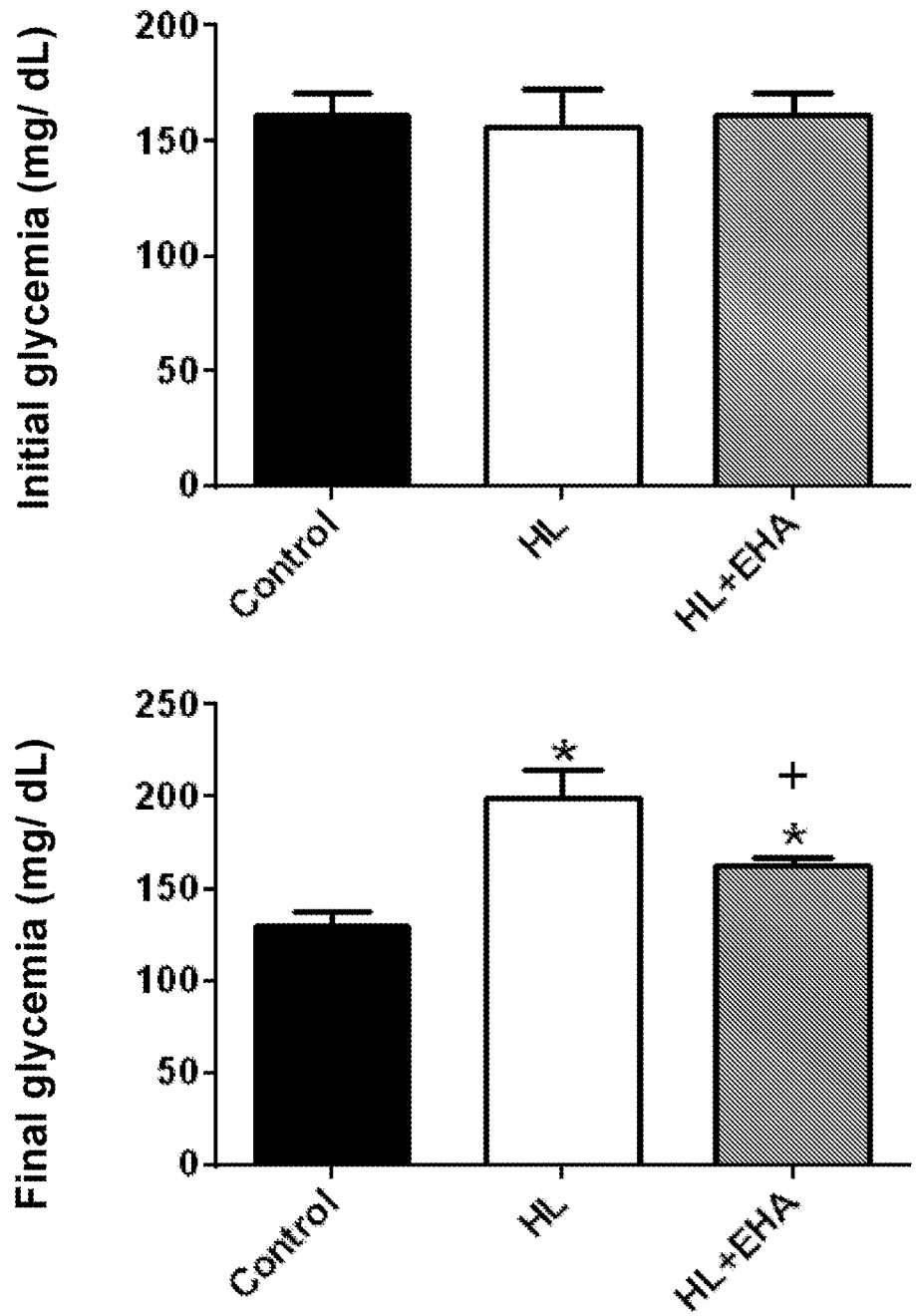

FIG. 8e shows that the increase in plasma glucose/glycemia levels induced by the hyper-lipid diet over 90 days in C57BL/6 mice is significantly reduced by the action of EHA at the dose of 300 mg/kg/day applied by gastric gavage. Values are expressed as mean±standard error of the mean, n=9 male mice in the control and HL groups; n=12 mice in the HL+EHA group. Significant differences between groups are indicated by the symbols: "*" p<0.05 in relation to the control group; "+" p<0.05 compared to the HL group; as determined by the one-way ANOVA method and Tukey's post-test.

Figure 8F:
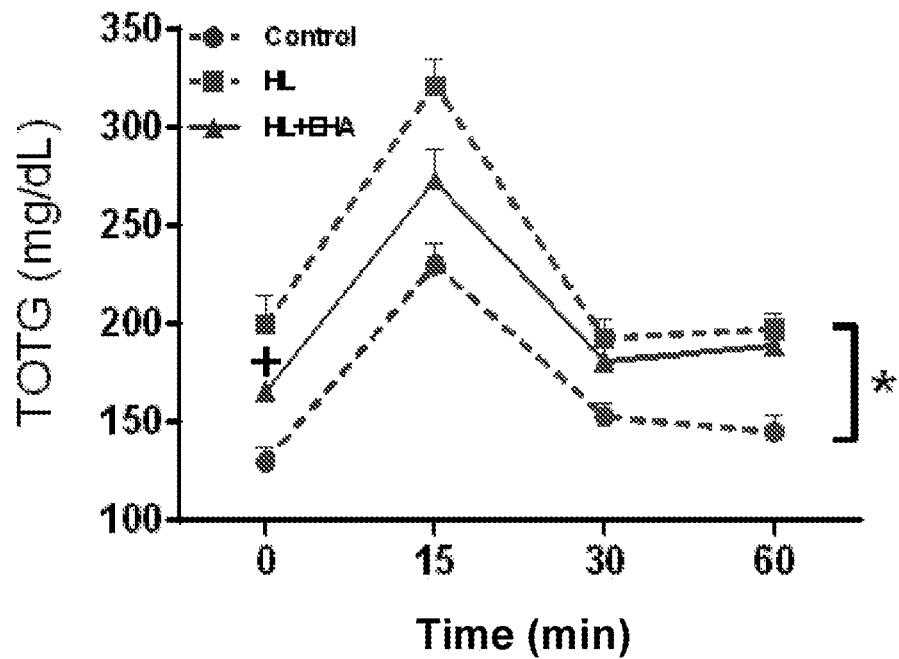
Figure 8F:
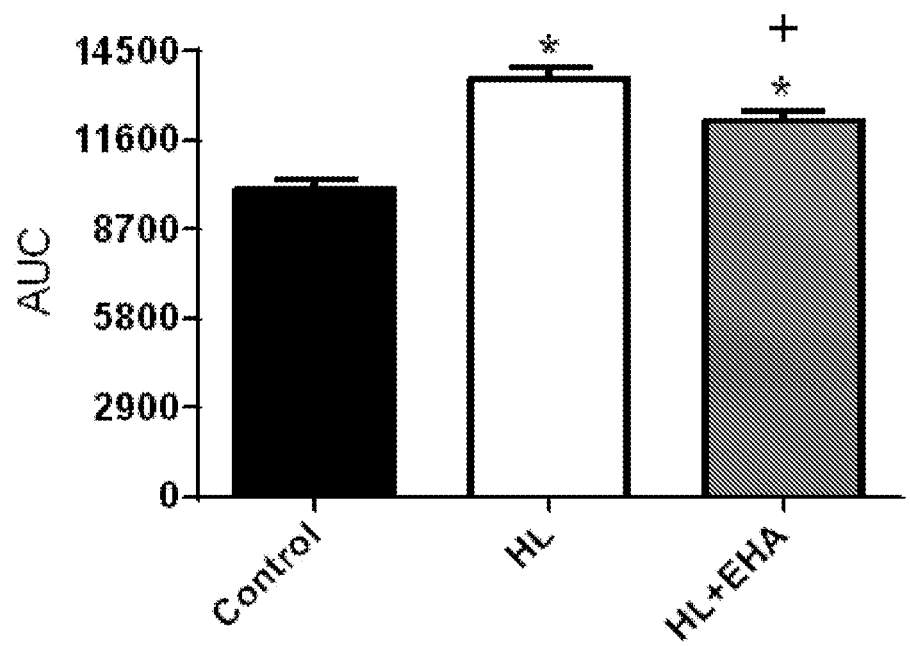

FIG. 8f shows that the increase in the Oral Glucose Tolerance Test (OGTT) induced by the hyper-lipid diet over 90 days in C57BL/6 mice is significantly reduced by the action of EHA at the dose of 300 mg/kg/day applied by gavage gastric, AUC (Area Under the Curve). Values are expressed as mean±standard error of the mean, n=9 male mice in the control and HL groups; n=12 mice in the HL+EHA group. Significant differences between groups are indicated by the symbols: "*" p<0.05 in relation to the control group; "+" p<0.05 compared to the HL group; as determined by the one-way ANOVA method and Tukey's post-test.

Figure 8G:
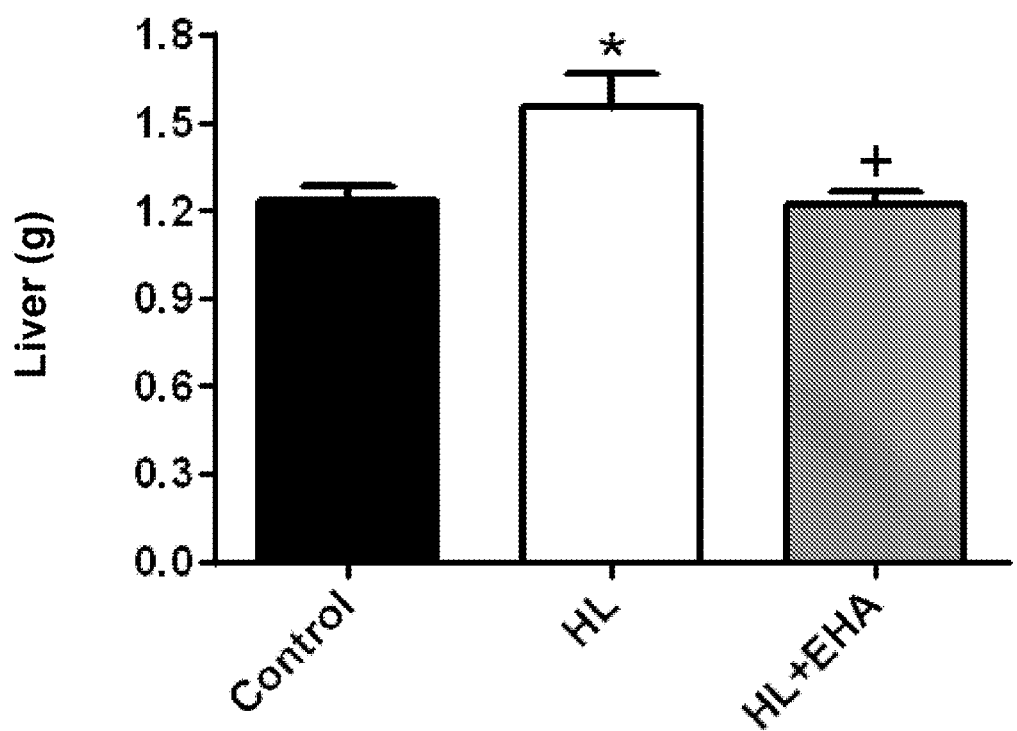

FIG. 8g shows that the increase in liver weight observed in C57BL/6 mice undergoing a hyper-lipid diet for 90 days is significantly inhibited by gastric gavage of EHA over 90 days. Values are expressed as mean±standard error of the mean, n=9 male mice in the control and HL groups; n=12 mice in the HL+EHA group. Significant differences between groups are indicated by the symbols: "*" p<0.05 in relation to the control group; "+" p<0.05 compared to the HL group; as determined by the one-way ANOVA method and Tukey's post-test.

Figure 8H:
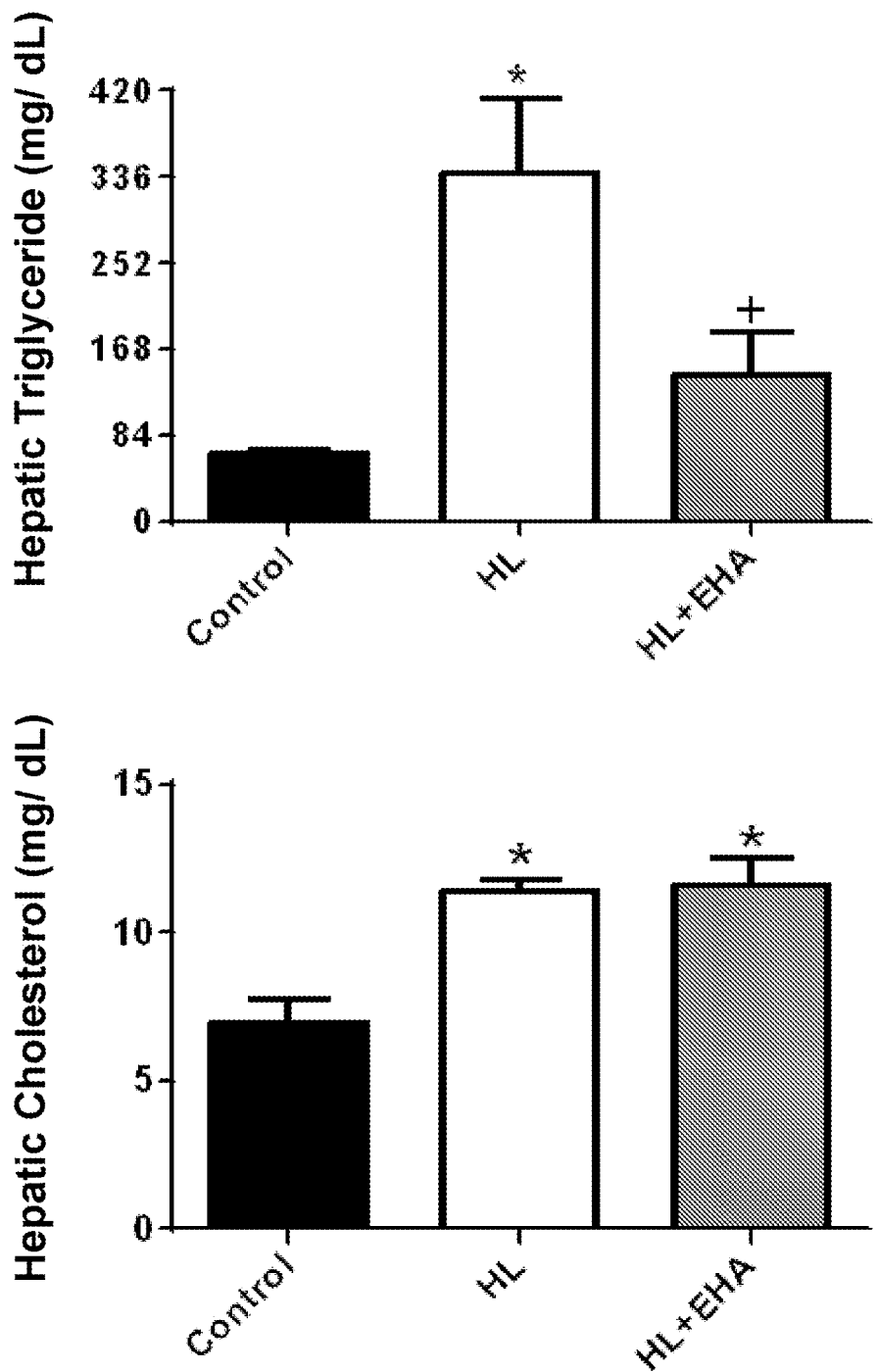

FIG. 8h shows that the increase in hepatic triglyceride (hepatic lipid profile) but not hepatic cholesterol, observed in C57BL/6 mice submitted to a hyper-lipid diet over 90 days is significantly inhibited by the intragastric administration of EHA dose of 300 mg/kg/day. Values are expressed as mean±standard error of the mean, n=9 male mice in the control and HL groups; n=12 mice in the HL+EHA group. Significant differences between groups are indicated by the symbols: "*" p<0.05 in relation to the control group; "+" p<0.05 compared to the HL group; as determined by the one-way ANOVA method and Tukey's post-test.

It should be understood that the preferred embodiments mentioned here are merely illustrative of the present invention. Numerous variations in design and use of the present invention may be contemplated in view of the following claims without straying from the intended scope and field of the invention herein disclosed.

What is claimed is:

1. A process for obtaining an acai berry seed extract comprising:
    (a) milling dried acai berry seed in a knife mill, obtaining a powder;

(b) macerating the powder obtained in (a) in an ethanol hydroalcoholic solution producing a solid residue;
(c) separating the solid residue by vacuum filtration, obtaining the acai berry seed extract; and
(d) optionally drying of the extract;
wherein in (b) the dried and milled acai berry seeds of (a) are extracted with 70% ethanol hydroalcoholic solution in a dispersing device for 3 times, for 3 minutes each time, and in (c) the separation is by vacuum filtration in a porous plate funnel.

2. The process according to claim 1, wherein the extract is dried, said process further comprising:
(e) solubilizing the dried acai berry seed extract obtained in (d) in distilled water to obtain an aqueous phase;
(f) transferring the aqueous phase to a separator funnel;
(g) adding to the aqueous phase in (f) at least one protic polar solvent proceeding a further extraction resulting in a phase separation; and
(h) after separation of the phases, evaporate the solid residue phase under vacuum until complete drying to obtain at least one fraction of the acai berry seed extract.

3. The process according to claim 2, wherein the protic polar solvent is selected from the group consisting of hexane, ethyl acetate, acetate, butanol, water, and combinations thereof.

4. The process according to claim 1, wherein the acai berry seed extract obtained by the process comprises a component selected from the group consisting of procyanidin B2, epicatechin, rutin, catechin, vicenine 2, vitexin, and chlorogenic acid.

5. The process according to claim 2, wherein the at least one fraction of the açai berry seed extract obtained by the process comprises a component selected from the group consisting of procyanidin B2, epicatechin, rutin, catechin, vicenine 2, vitexin, and chlorogenic acid.

\* \* \* \* \*